United States Patent

Kuszmann et al.

[11] 4,235,803
[45] Nov. 25, 1980

[54] 1,6-DIMESYL-3,4-DIMETHYL-D-MANNITOL AND A PROCESS FOR THE PREPARATION THEREOF

[75] Inventors: Janos Kuszmann; Pal Sohar; Endre Csanyi; Emilia Kiraly nee Vida, all of Budapest, Hungary

[73] Assignee: Gyogyszerkutato Intezet, Budapest, Hungary

[21] Appl. No.: 33,492

[22] Filed: Apr. 26, 1979

[30] Foreign Application Priority Data

May 3, 1978 [HU] Hungary .............................. GO-1402

[51] Int. Cl.³ ............................................ C07C 143/68
[52] U.S. Cl. ................................... 260/456 R; 424/303
[58] Field of Search ...................... 260/456 R; 424/303

[56] References Cited

FOREIGN PATENT DOCUMENTS 891466  3/1962 United Kingdom ................. 260/456 R
945990  1/1964 United Kingdom ................. 260/456 R

*Primary Examiner*—Nicky Chan
*Attorney, Agent, or Firm*—Young & Thompson

[57] ABSTRACT

The invention relates to 1,6-dimesyl-3,4-dimethyl-D-mannitol of the formula (I),

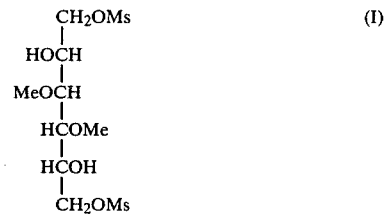

wherein Ms is mesyl and Me is methyl. This compound is a potent cytostatic agent which can be used to advantage in the therapy of various tumorous diseases.

1,6-Dimesyl-3,4-dimethyl-D-mannitol is prepared according to the invention by subjecting 3,4-dimethyl-D-mannitol to partial mesylation followed by acylation, and splitting off the acyl groups of the resulting compound of the general formula (III),

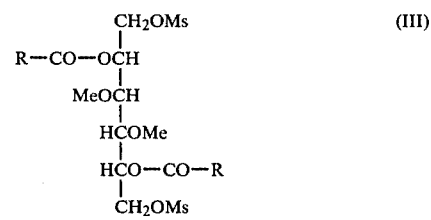

wherein Ms and Me are as defined above and R is a saturated lower aliphatic group, with an acidic alcohol.

1 Claim, No Drawings

1,6-DIMESYL-3,4-DIMETHYL-D-MANNITOL AND A PROCESS FOR THE PREPARATION THEREOF

The invention relates to 1,6-dimesyl-3,4-dimethyl-D-mannitol of the formula (I),

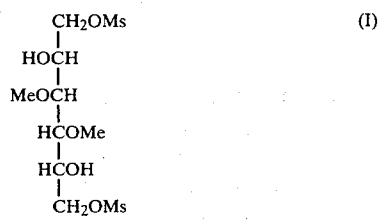

wherein Ms is mesyl and Me is methyl, and pharmaceutical compositions containing the same, furthermore to a process for the preparation thereof.

The compound of formula (I) has not been described so far in the literature. The analogous compound with a cyclic ether group in position 3,4 (i.e. the 3,4-O-isopropylidene derivative containing a dioxolane ring) is described in Naturwissenschaften 46, 84 (1959) and Acta Chim. Hung. 25, 361–368 (1960). Biological examinations have shown, however, that 3,4-O-isopropylidene-hexitols containing cytostatic groups in positions 1 and 6 are ineffective (Chem. Ber. 92 2506–2515 /1959/; Arzneimittelforschung 17, 145–149 /1967/).

Now it has been found, unexpectedly, that 1,6-dimesyl-3,4-dimethyl-D-mannitol of the formula (I) is an extremely potent cytostatic agent, being even more effective than 1,6-dimesyl-D-mannitol which contains free hydroxy groups (Mannogranol[R]), 1,6-dibromo-1,6-dideoxy-D-mannitol (Myelobromol[R]) and 1,6-dibromo-1,6-dideoxy-dulcitol (Elobromol[R]), the most active of the commercially available cytostatics of this series.

Our tests were performed on various transplantable mouse and rat tumors. The following tumor strains were applied:

| | | |
|---|---|---|
| Mouse: | SC-180 sc. sarcoma | (solid) |
| | Harding-Passey melanoma | " |
| | NK/Lymphoma | (ascites) |
| | Ehrlich carcinoma | " |
| | P-388 | (leukaemia) |
| Rat: | Yoshida sc. sarcoma | (solid) |
| | Walker sc. carcino-sarcoma | " |

The animal strains involved in the tests were as follows:

| |
|---|
| CFY rats |
| CFLP mice |
| BDF₁ mice (L-1210, P-388) |

The tests were always performed on animals of both sexes. At the beginning of the tests the average body weight of mice was 20 to 22 g, whereas that of rats 150 to 180 g. The animals were kept in plastic cages and fed with a standard laboratory animal feed (LATI, Gödöllő, Hungary). The animals received water ad libitum.

Solid tumors were transplanted by a subcutaneous implantation of tumor chips. Ascites type tumors were transplanted with 10⁷ cells received from the ascites, whereas leukaemia type tumors were transplanted with spleen suspension. The treatment of the animals was started 24 hours after transplantation, with the only exception of Harding-Passey melanoma, when treatment was started on the 4th day after transplantation. The results are listed in Tables 1 to 3.

TABLE 1

Comparison of the $ED_{50}$ values on Yoshida sc. sarcoma of rats

| | $ED_{50}$ | | Relative activity | |
|---|---|---|---|---|
| Compound | i.p. | p.o. | i.p. | p.o. |
| 1,6-Dimesyl-3,4-dimethyl-mannitol | 20 | 70 | 1 | 1 |
| 1,6-Dibromo-1,6-dideoxy-D-mannitol (Myelobromol) | 490 | 170 | 0.04 | 0.41 |
| 1,6-Dimesyl-D-mannitol (Mannogranol) | 500 | 600 | 0.04 | 0.116 |
| 1,6-Dibromo-1,6-dideoxy-dulcitol (Elobromol) | 50 | — | 0.4 | — |

TABLE 2

Tumor inhibiting effect on solid tumors

| Tumor | Compound | Dosage mg/kg | Treatment | Inhibition |
|---|---|---|---|---|
| Walker sc. sarcoma | 1,6-Dimesyl-3,4-dimethyl-D-mannitol | 10 | 5 × i.p. | 90 |
| | | 10 | 5 × p.o. | 97 |
| | 1,6-Dibromo-1,6-dideoxy-dulcitol | 100 | 6 × i.p. | 95** |
| S-180 sc. sarcoma | 1,6-Dimesyl-3,4-dimethyl-D-mannitol | 100 | 4 × p.o. | 50 |
| | | 200 | 6 × p.o. | 70 |
| | 1,6-Dibromo-1,6-dideoxy-dulcitol | 200 | 8 × i.p. | 57** |
| | 1,6-dimesyl-1,6-dideoxy-D-mannitol | 300 | 6 × i.p. | 31 |
| | | 500 | 6 × i.p. | toxic |
| Harding-P. melanoma | 1,6-Dimesyl-3,4-dimethyl-D-mannitol | 30 | 10 × p.o. | 31 |
| | | 100 | 10 × p.o. | 52 |
| | 1,6-Dibromo-1,6-dideoxy-dulcitol | 200 | 13 × i.p. | 67 |

*Performed on groups of 8 animals
**Németh et al.: Cancer Chemother. Rep. 56, 593–602 (1972)

$$\text{Inhibition \%} = \frac{\text{tumor weight of treated animals} \times 100}{\text{tumor weight of control animals}}$$

TABLE 3

Tumor inhibiting effect on ascites and leukaemia type tumors

| Tumor | Compound | Dosage mg/kg | Treatment | Prol. of life span % | Healing |
|---|---|---|---|---|---|
| NK/Ly lymphoma | 1,6-Dimesyl-3,4-dimethyl-D-mannitol | 30 | 4 × i.p. | 101 | |
| | 1,6-Dibromo-1,6-dideoxy-dulcitol | 125 | 6 × i.p. | 90** | |
| Ehrlich asc. carcinoma | 1,6-Dimesyl-3,4-dimethyl-D-mannitol | 100 | 4 × i.p. | 99.6 | |
| P-388 leukaemia | 1,6-Dimesyl-3,4-dimethyl-D-mannitol | 100 | 4 × i.p. | 82 | 0/8 |

**Németh et al.: Cancer Chemother. Rep. 56, 593–602 (1972)

Healing = tumor-free survival of 90 days after transplantation

Prolongation of life span (%) = $\frac{\text{life span of treated animals} \times 100}{\text{life span of control animals}}$ The data of Tables 1 to 3 show that the compound of formula (I) significantly inhibits the growth of solid tumors. On these tumors the compound exerts a significant inhibition even in very low dosages compared to the toxic one, giving very favourable therapeutical indices ($LD_{50}/ED_{50}$).

Since the toxicities of the test compound and the reference substances are of the same order of magnitude, relative activity values can be calculated by comparing the $ED_{50}$ values (see Table 1). The results of these calculations also indicate unambiguously the high superiority of the compound of formula (I).

The compound of formula (I), like the reference substances, possesses a weak antileukaemic effect. On Ehrlich ascites tumor the compound of formula (I) exerted, however, a healing effect (see Table 3), whereas the reference substance had only a medium inhibiting effect.

The acute toxicity ($LD_{50}$ value) of the compound of formula (I), determined on CFLP and $BDF_1$ mice, was 1000 mg/kg after intraperitoneal administration and 1100 mg/kg after oral administration, which proves the excellent oral resorption of the compound in question. The tests were performed on groups consisting of 10 mice (5 males and 5 females), and the animals were kept under observation for 3 weeks. Of the reference substances the $LD_{50}$ value of e.g. 1,6-dibromo-1,6-dideoxy-dulcitol determined on the same animals was 900 mg/kg (i.p.) and 1500 mg/kg (p.o.), respectively (Németh et al.: Cancer Chemother. Rep. 56, 593–602 /1972/).

1,6-Dibromo-1,6-dideoxy-D-mannitol, 1,6-dimesyl-D-mannitol and 1,6-dibromo-1,6-dideoxy-dulcitol, applied as reference substances, exert a characteristic effect on haematopoiesis. This effect is eventually a rather strong and selective action on the formation of myeloid leukocytes. Examining the compound of formula (I) in this respect we found that its haematopoietic activity is weak, and, in contrast to the above, the effect is not selective. The results observed in the examination of peripheral blood count on rats are listed in Table 4.

TABLE 4

| | Effect on peripheral blood count of rats | | | |
| --- | --- | --- | --- | --- |
| Dosage mg/kg | Maximum decrease in granulocyte count, % | Duration of the effect, days | Maximum decrease in lymphocyte count, % | Duration of the effect, days |
| 30 | 38.8 | 1 | 26 | 2 |
| 100 | 38.8 | 1 | 47 | 5 |
| 300 | 52.1 | 3 (4–7) | 38 | 5 |

The test results listed above indicate that the compound of formula (I) is a substance of strong cytostatic effect, low toxicity, applicable with a high security.

The process for the preparation of the compound of formula (I) is based on the recognition that the O-acyl groups in position 2 and 5 of a crystalline mixed ester having the general formula (III),

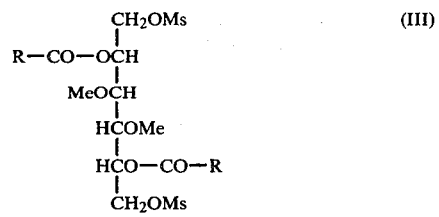

wherein Ms and Me are as defined above and R is a saturated lower aliphatic group, can be split off selectively by treating it with an acidic alcohol. The compounds of the general formula (III) can be prepared by subjecting 3,4-di-O-methyl-D-mannitol (Am. Chem. Soc. 76, 2701–2705 /1974/; J. Org. Chem. 33, 3714–3718 /1968/) of the formula (II),

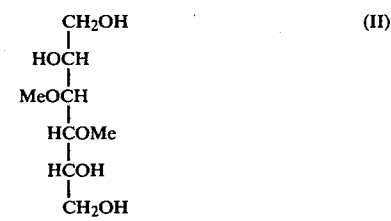

wherein Me is as defined above, to partial mesylation followed by acylation.

Thus the compound of formula (I) is prepared according to the invention so that the mannitol derivative of the formula (II) is subjected to partial mesylation followed by acylation, and the resulting compound of the general formula (III), wherein R is a saturated lower aliphatic group, is deacylated with an acidic alcohol.

According to a preferred method of the invention one proceeds as follows: 3,4-di-O-methyl-D-mannitol, a compound which can be prepared easily by methods reported in the literature (Am. Chem. Soc. 76, 2701–2705 /1954/; J. Org. Chem. 33, 3714–3718 /1968/) is dissolved in pyridine, and 2.2 equivalents of mesyl chloride are added to the cooled solution. At the end of the reaction 3 equivalents of acetic anhydride are introduced. The resulting ester (formula /III/, R=$CH_3$) is isolated by pouring the reaction mixture into water and extracting the resulting mixture with chloroform. The substance, obtained after evaporating the chloroform solution, is boiled on a steam bath in the presence of methanol containing dry gaseous hydrochloric acid in order to split off the acetyl groups. At the end of the reaction the solution is evaporated, and the resulting crude product is recrystallized from ethanol. In this way 1,6-di-O-mesyl-3,4-di-O-methyl-D-mannitol is obtained with a good yield.

The compound of the formula (I) can be converted into pharmaceutical compositions for enteral or parenteral administration (such as tablets, capsules, injectable solutions, suspensions, etc.) by methods known per se, utilizing conventional pharmaceutical carriers, diluents, additives and/or auxiliary agents.

The invention is elucidated in detail by the aid of the following non-limiting Examples.

EXAMPLE 1

Preparation of 1,6-di-O-mesyl-3,4-di-O-methyl-D-mannitol

Step A: Preparation of 1,6-di-O-mesyl-2,5-di-O-acetyl-3,4-di-O-methyl-D-mannitol (formula /III/, R=CH₃)

105 g of crystalline, 3,4-dimethyl-D-mannitol of formula (II) (Am. Chem. Soc. 76, 2701–2705 /1954/; J. Org. Chem. 33, 3714–3718 /1968/) are dissolved in 1500 ml of absolute pyridine. The solution is cooled to −10° C., and 85 ml of mesyl chloride are added dropwise to the cooled and vigorously stirred solution within one hour. Thereafter the temperature of the mixture is raised to 0° C., and the mixture is maintained at this temperature for further 30 minutes. The resulting suspension is cooled again, and 150 ml of acetic anhydride are introduced under stirring at such a rate that the temperature of the mixture does not raise above 0° C. The resulting mixture is maintained at 0° C. overnight, then it is poured onto 5 liters of icy water. The separated oil is taken up in 1 liter of chloroform, and the aqueous phase is extracted thrice with 200 ml of chloroform each. The organic extracts are combined, washed with ice-cold 1 n aqueous sulfuric acid solution until the wash remains acidic, then with water, ice-cold 5% aqueous sodium hydrocarbonate solution and again with water. The solution is dried over sodium sulfate and then evaporated. The solid residue is dissolved in twofold volume of warm ethyl acetate, and petroleum ether is added to the solution until it becomes turbid. The mixture is cooled, the separated substance is filtered off and washed with petroleum ether. 161 g (71.5%) of a crude product, melting at 99°–101° C., are obtained, which is sufficiently pure to use it in the next step. When recrystallized from a threefold volume of ethanol a pure substance, melting at 101°–103° C., is obtained. $[\alpha]_D^{20} = +18.7°$ (c=1, in chloroform); $R_f = 0.5$ (run in a 1:2 mixture of carbon tetrachloride and ethyl acetate).

Analysis: calculated for $C_{14}H_{26}O_{12}S_2$ (M. wt.: 450.48): C: 37.33%, H: 5.82%, S: 14.24%; found: C: 37.45%, H: 5.91%, S: 14.43%.

Step B: Preparation of 1,6-di-O-mesyl-3,4-di-O-methyl-D-mannitol (formula /I/)

45 g of the crude product (formula /III/, R=CH₃) obtained according to step A are suspended in 450 ml of 7.5 n dry methanolic hydrochloric acid, and the suspension is refluxed on a steam bath. When dissolution is complete the boiling is continued for additional 10 minutes, then the solution is evaporated to dryness in vacuo. The residue is suspended in a small amount of ethanol, and the solid is filtered off. 25 g (68%) of the title compound are obtained; m.p.: 99°–102° C. This product is recrystallized from a sevenfold volume of ethanol to obtain 22 g (60%) of pure 1,6-di-O-mesyl-3,4-di-O-methyl-D-mannitol; m.p.: 112°–114° C., $[\alpha]_D^{20} = +35°$ (c=1, in methanol).

Analysis: calculated for $C_{10}H_{22}O_{10}S_2$ (M. wt.: 366.41): C: 32.78%, H: 6.05%, S: 17.50%; found: C: 32.81%, H: 6.08%, S: 17.65%.

EXAMPLE 2

Preparation of pharmaceutical compositions (A) Tablets

Orally administerable tablets for therapeutical purposes, containing 250 mg of active agent each, are prepared with the following composition:

| | |
|---|---|
| 1,6-di-O-mesyl-3,4-di-O-methyl-D-mannitol | 250 mg |
| lactose | 50 mg |
| corn starch | 180 mg |
| polyvinylpyrrolidone | 10 mg |
| colloidal silica | 5 mg |
| magnesium stearate | 5 mg |
| average weight: | 500 mg |

The tablets are provided with film coating or sugar coating.

(B) Injections 200 mg of powdered 1,6-di-O-mesyl-3,4-di-O-methyl-D-mannitol are filled into a glass vial of 5 ml volume, and the vial is sealed with a rubber stopper. Before administration the contents of the vial are dissolved in 3 ml of distilled water for injection purposes.

What we claim is:

1. 1,6-Dimesyl-3,4-dimethyl-D-mannitol of the formula (I),

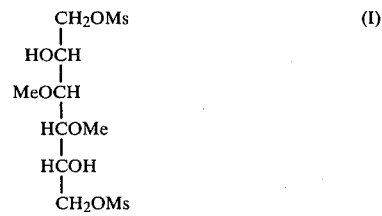

wherein Ms is mesyl and Me is methyl.

* * * * *